(12) United States Patent
Acemoglu et al.

(10) Patent No.: US 7,709,657 B2
(45) Date of Patent: May 4, 2010

(54) PROCESS FOR THE SYNTHESIS OF ORGANIC COMPOUNDS

(75) Inventors: Murat Acemoglu, Basel (CH); Berthold Schenkel, Weil am Rhein (DE); Wen-Chung Shieh, Berkeley Heights, NJ (US); Song Xue, Parsippany, NJ (US); Erich Widmer, Münchenstein (CH); Pedro Garcia Fuentes, Lorca (ES); Jose Martin Medina, La Ñora (ES); Francisco Vicente Baños, Las Torres de Cotillas (ES)

(73) Assignee: Novartis AG, Basel (CH)

( * ) Notice: Subject to any disclaimer, the term of this patent is extended or adjusted under 35 U.S.C. 154(b) by 235 days.

(21) Appl. No.: 11/915,658

(22) PCT Filed: Jun. 7, 2006

(86) PCT No.: PCT/US2006/022026

§ 371 (c)(1),
(2), (4) Date: Nov. 27, 2007

(87) PCT Pub. No.: WO2006/135619

PCT Pub. Date: Dec. 21, 2006

(65) Prior Publication Data

US 2008/0200691 A1 Aug. 21, 2008

Related U.S. Application Data

(60) Provisional application No. 60/688,920, filed on Jun. 9, 2005.

(51) Int. Cl.
*C07D 233/61* (2006.01)
(52) U.S. Cl. .................................. 548/335.5
(58) Field of Classification Search ............... 548/335.5
See application file for complete search history.

(56) References Cited

U.S. PATENT DOCUMENTS

| | | | |
|---|---|---|---|
| 6,323,366 B1 | 11/2001 | Wolfe et al. | |
| 6,395,916 B1 | 5/2002 | Buchwald et al. | |
| 7,169,791 B2 * | 1/2007 | Breitenstein et al. | 514/275 |
| 2003/0236413 A1 | 12/2003 | Cellier et al. | |

FOREIGN PATENT DOCUMENTS

| WO | WO 00/05199 | 2/2000 |
|---|---|---|
| WO | WO 2004/005281 | 1/2004 |

OTHER PUBLICATIONS

Klapars et al., "A General and Efficient Copper Catalyst for the Amidation of Aryl Halides and the N-Arylation of Nitrogen Heterocycles," J. Am. Chem. Soc., vol. 123, pp. 7727-7729 (2001).
Suzuki et al., "A Novel Non-Acidic Method for the Preparation of 2,2,2-Trifluoro-1-(3-nitrophenyl)ethanone and 1-Nitro-3-trifluoromethylbenzene, Versatile Starting Materials for trifluoromethyl-Containing Aromatic Compounds," Synthesis, pp. 1353-1354 (1995).
Wolfe et al., "Room Temperature Catalytic Amination of Aryl Iodides," J. Org. Chem., vol. 62, pp. 6066-6068 (1997).
Kiyomori et al., "An Efficient Copper-Catalyzed Coupling of Aryl Halides with Imidazoles," Tetrahedron Letters, vol. 40, pp. 2657-2660 (1999).
Baenziger et al., "Practical Synthesis of 8α-Amino-2,6-dimethylergoline: An Industrial Perspective," Organic Process Research & Development, vol. 1, pp. 395-406 (1997).
Zilberman J., "One-Step Preparation of some 3-Substituted Anisoles," Organic Process Research & Development, vol. 7, pp. 303-305 (2003).
Purohit et al., "Synthesis and Characterization of Oligodeoxynucleotides Containing the Major DNA Adducts Formed by 1,6- and 1,8-Dinitropyrene," Organic Letters, Vol. 2, No. 13, pp. 1871-1874 (2000).
Ali et al., "An Improved Method for the Palladium-Catalyzed Amination of Aryl Iodides," J. Org. Chem., vol. 66, pp. 2560-2565 (2001).
Mukkanti et al., "Selective and Squential Reduction of Nitroaromatics by Montmorillonitesilylaminepalladium(II) Complex," Tetrahedron Letters, vol. 30, No. 2, pp. 251-252 (1989).
Subba Rao et al., "Efficient selective hydrodebromination of aryl bromides by montmorillonitesilylaminepalladium(II) chloride," Journal of Organometallic Chemistry, vol. 367, Issue 3, pp. C29-C31 (1989) Abstract only.
Grondard et al., "Convenient Syntheses of Racemic 2-(3-Nitrophenyl)Propanoic Acid and 2-(3-Aminophenyl)Propanoic Acid," Synthetic Communications, vol. 27(3), pp. 425-430 (1997).
Shackelford et al., "Electrophilic tetraalkylammonium Nitrate Nitration. II. Improved Anhydrous Aromatic and Heteroaromatic Mononitration with Tetramethylammonium Nitrate and Triflic Anhydride, Including Selected Microwave Examples," J. Org. Chem., vol. 68, pp. 267-275 (2003).

(Continued)

*Primary Examiner*—Kamal A Saeed
(74) *Attorney, Agent, or Firm*—Matthew Mulkeen

(57) ABSTRACT

The present invention provides an efficient, safe and cost effective way to prepare 5-(4-methyl-1H-imidazol-1-yl)-3-(trifluoromethyl)-benzenamine which is an intermediate for the preparation of substituted pyrimidinylaminobenzamides of formula (II):

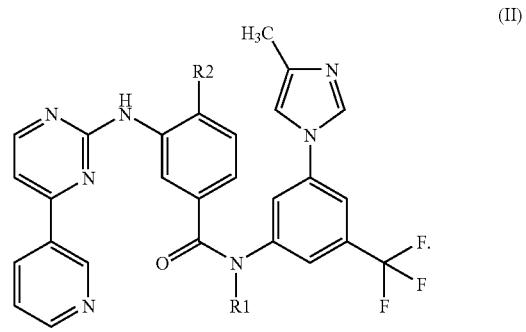

10 Claims, No Drawings

OTHER PUBLICATIONS

Mellor et al., "Improved Nitrations Using Metal Nitrate—Sulfuric Acid System," Tetrahedron, vol. 56, pp. 8019-8024 (2000).
Zoltewicz, J.A., "New Directions in Aromatic Nucleophilic Substitution," Topics in Current Chemistry, vol. 59, pp. 33-64 (1975).
Hofmann, A., Helv. Chim. Acta, vol. XXX, Fasciculus I, pp. 44-51 (1947).
Möller F., in Houben-Weyl. Bd. 11/1, pp. 854 (1957).
Hofmann, A.W., Chem. Ber. 14, pp. 275 (1881).

* cited by examiner

PROCESS FOR THE SYNTHESIS OF ORGANIC COMPOUNDS

This application claims benefit of U.S. Provisional Application No. 60/688,920, filed Jun. 9, 2005.

BACKGROUND OF THE INVENTION

The present invention provides an efficient, safe and cost effective way to prepare 5-(4-methyl-1H-imidazol-1-yl)-3-(trifluoromethyl)-benzenamine of the following formula (I):

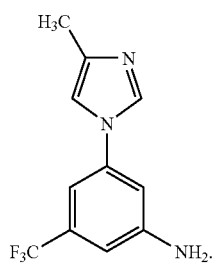

The compound of formula (I) is an intermediate for the preparation of substituted pyrimidinylaminobenzamides of formula (II):

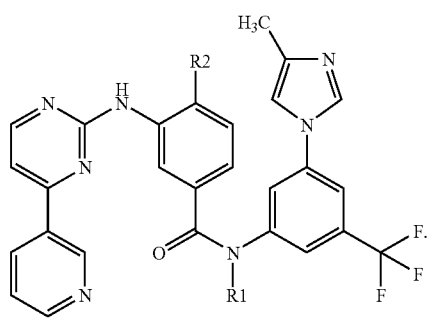

Compounds of formula (II) have been disclosed in W. Breitenstein et al., WO 04/005281 A1, the disclosure of which is incorporated herein by reference. These compounds have been shown to inhibit one or more tyrosine kinases, such as c-Abl, Bcr-Abl, the receptor tyrosine kinases PDGF-R, Flt3, VEGF-R, EGF-R and c-Kit. As such, compounds of formula (II) can be used for the treatment of certain neoplastic diseases, such as leukemia.

Previous synthesis of compound (I) involves a 4 step synthetic route starting with an aromatic substitution reaction of compound (IIIa), 4-methyl-1H-imidazole, with compound (IV), which requires employing high energy (150° C.) (Scheme 1).

Scheme 1

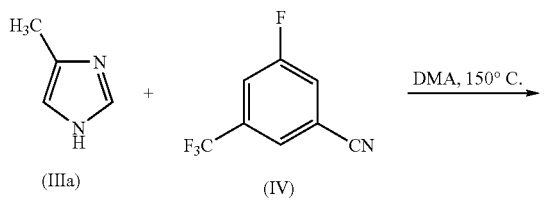

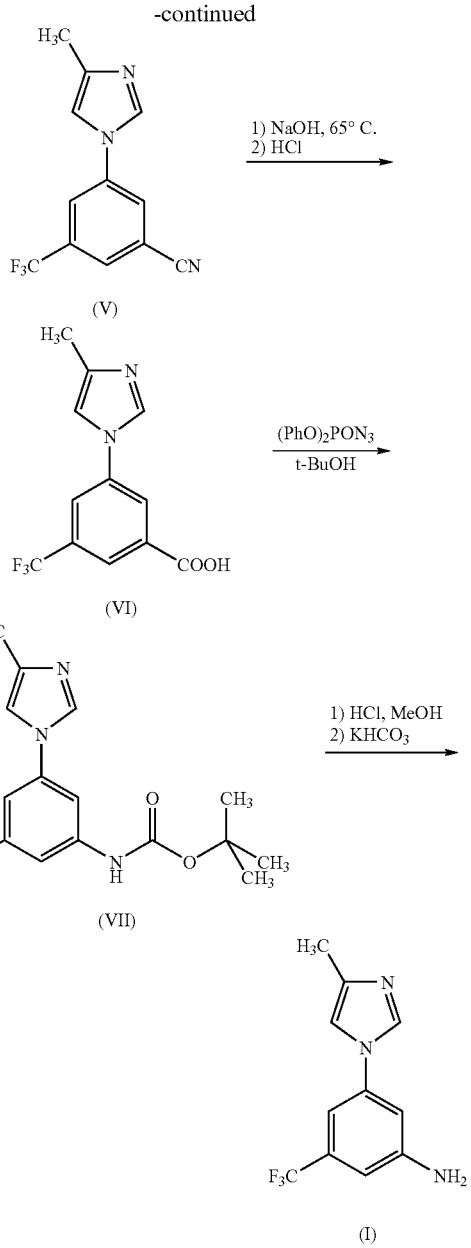

Furthermore, transformation of compound (VI) to compound (VII) via Curtius rearrangement utilizes an unsafe reagent, diphenylphosphorylazide. This reaction produces inconsistent product yields and quality. In addition, removing the resulting diphenylphosphoric acid by-product is difficult. The carbamate product (VII) needs to be purified by chromatography, which is expensive and time consuming for commercial operations.

It is an object of this invention to provide alternative processes to make the compound of formula (I) efficiently and in high yields.

It is a further object of this invention to make compound (I) from lower cost starting materials and reagents.

It is a still further object of this invention to provide for a process to make the compound of formula (I) using safer reagents.

The present invention overcomes the problems of the reaction shown in Scheme 1 above.

SUMMARY OF THE INVENTION

The present invention provides novel synthetic processes for the manufacture of 5-(4-methyl-1H-imidazol-1-yl)-3-(trifluoromethyl)-benzenamine having formula (I):

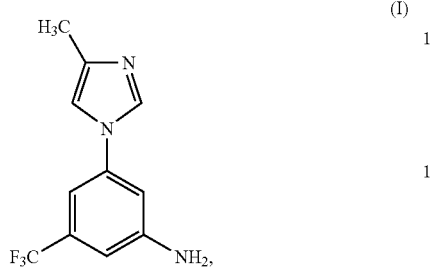

(I)

The compound of formula (I) is an intermediate for the preparation of substituted pyrimidinylaminobenzamides of formula (II) which have been disclosed in W. Breitenstein et al, WO 04/005281, which published on Jan. 15, 2004, the disclosure of which is incorporated by reference. A preferred compound of formula (II) is 4-methyl-3-[[4-(3-pyridinyl)-2-pyrimidinyl]amino]-N-[5-(4-methyl-1H-imidazol-1-yl)-3-(trifluoromethyl)phenyl]benzamide.

DETAILED DESCRIPTION OF THE INVENTION

The general reaction scheme of the invention can be illustrated in the following embodiments:

In a first embodiment, the present invention provides the general process of making compound (I) as follows:

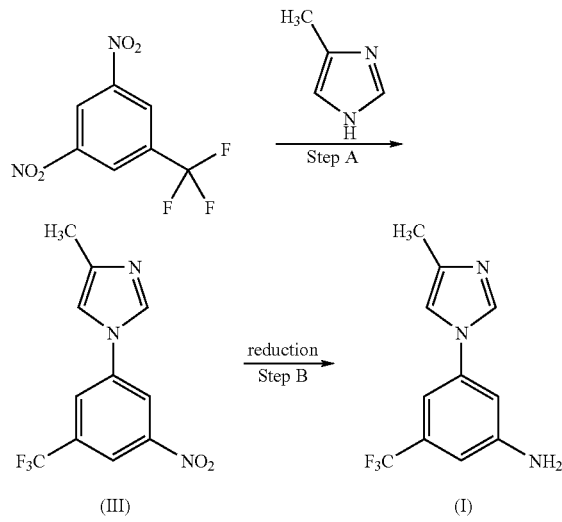

Step A involves a base and nucleophilic aromatic substitution for the synthesis of 4-methyl-1-(3-nitro-5-trifluoromethyl-phenyl)-1H-imidazole (III). Step B is a reduction leading to compound (I).

The base may be selected from an alkoxide, a hydride, a carbonate or a phosphate. Preferably the base is a potassium alkoxide, sodium alkoxide, sodium hydride, potassium carbonate or potassium phosphate. The solvent used in Step A is selected from N,N-dimethylformamide (DMF), N,N-dimethylacetamide (DMA), or 1-methyl-2-pyrrolidinone (NMP) or mixtures thereof.

A second embodiment involves coupling of dinitrobenzotrifluoride and 4-methyl-1H-imidazole followed by a hydrogenation reaction.

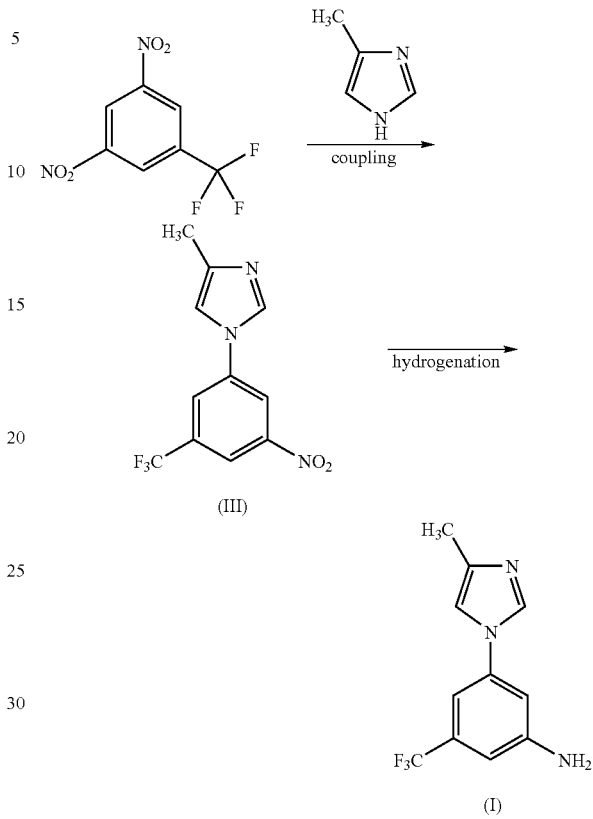

In addition, a third embodiment involves a further step for each of the process described above optionally involving the transformation of compound (III) into a salt of the formula (IV), for purification reasons, as illustrated by the following scheme:

Scheme 7

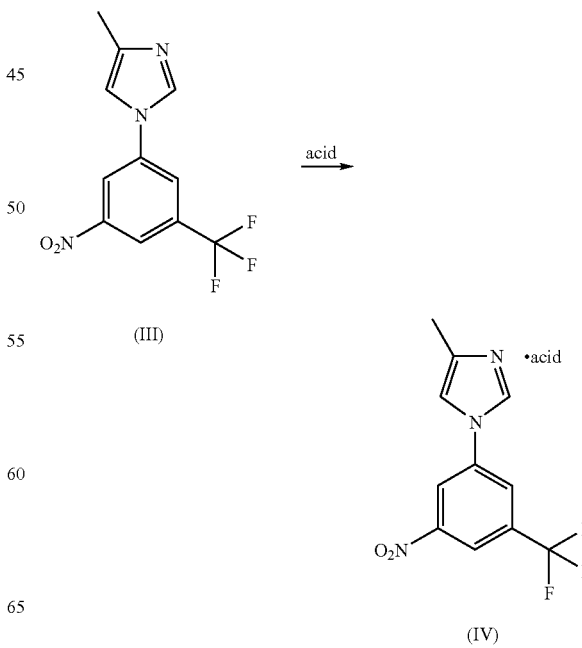

Here a solution of compound (III) is treated with an acid, or a solution thereof in water or an organic solvent, followed by isolation of the salt (IV), e.g., by filtration.

Compound (III) may then be obtained by treating salt (IV) with a base, preferably with aqueous sodium hydroxide solution, and isolating the free base (III) by extraction or crystallization.

The coupling reaction works in several common polar aprotic solvents, including dimethyl sulfoxide (DMSO), DMF, diglyme, THF, NMP and DMA.

It has been found, in accordance with the present invention that the coupling reaction of methylimidazole and dinitrobenzotrifluoride works better in DMA as the solvent, at a temperature in the range of 80-150° C., preferably 90-140° C. When $K_2CO_3$ or other bases are present, decomposition happens quite fast. Since the reaction mixture is not stable, reaction temperature and time should be reduced as much as possible. A faster heating and cooling cycle or shorter reaction time intervals, e.g., using microwave or by additional heat exchanger capacity in batch vessels or by using continuous reaction equipment will lead to less decomposition and a cleaner reaction.

$K_3PO_4$ has a similar performance compared to $K_2CO_3$, but the reaction is faster in the second case. A crude yield of >40% can be obtained according to the procedure described herein.

Reduction of the nitroimidazol intermediate, compound (III), can be performed using hydrogen gas or hydrogen transfer agents such as formic acid or ammonium formate, in the presence of common supported transition Group VIII metal catalysts, such as palladium, platinum, nickel or any combination. The metal is incorporated on the support in an amount of from 0.1-20 weight percent, based on the total weight of the metal and support. A combination of catalysts may also be used. It is within the scope of the present invention that the catalyst may also include a promoter or a co-promoter. The preferred reduction process, hydrogenation, uses hydrogen gas and palladium catalyst. The hydrogenation is usually performed at hydrogen pressure ranging 1-20 bar, preferably 5-10 bar. The crude product can also be isolated as hydrochloride salt. The final purification is achieved by crystallization of the free base, compound (I).

The following examples more particularly illustrate the present invention, but do not limit the invention in any way.

EXAMPLE 1

In a 200 L vessel, 9 kg of dinitrobenzotrifluoride, 5.3 kg of potassium carbonate and 84.6 kg of DMA are placed. After 10 minutes, stirring for a good mixture (dark red color), 3.8 kg of 4-methyl-1H-imidazole is charged, and the mixture is heated under stirring to 95° C. for 15-20 hours until analysis shows no starting material. The dark red-brown mixture is cooled down to 30° C., poured onto water under good stirring, filtered and washed with water, to yield ca. 5 kg of crude product, as a dark-brown wet solid. Analysis shows 1:9 of the wrong isomer. This solid is treated with cyclohexane and charcoal under heating, then the mixture is clarified, the cake washed with hot cyclohexane. The combined filtrates are cooled down to room temperature and a beige solid precipitates. Expected yield: 2.6-3.6 kg; 25-35%.

EXAMPLE 2

Hydrogenation Using Pd/C Catalyst 34.4 g of the nitro intermediate (III), prepared according to Example 1, 1.72 g, 5% Pd/C and 217 mL of methanol were charged into a hydrogenation vessel. After usual inertization, hydrogenation was performed at 70-75° C. and 4.2-7.5 bar for 2 hours. Following reaction completion by gas chromatographic analyses, the catalyst was filtered off and then rinsed with methanol. The filtrates were combined and most of the solvents was distilled off under vacuum. 174 mL of methanol and 526 mL of acetone were added to the solid residue. After the addition of 17 g of aqueous hydrochloric acid, the hydrochloride salt precipitated out. The suspension was cooled down to −10° C. to −5° C. and stirred for 30 minutes. Then the salt was filtered and washed with 58 mL of acetone. 319 mL of methanol was added to the wet hydrochloride salt and the suspension was heated to 58-62 C. After the addition of 18 g of sodium bicarbonate and 756 g water, the solution is filtered and cooled to 3-7° C. The crystallized product, compound (I), was filtered, washed with water and dried under vacuum at 60-75° C. (yield: 19.1 g, 62% of theory, purity >99%).

EXAMPLE 3

The following involves a hydrogenation process using the Raney Nickel catalyst. The nitro intermediate (III) (7.5 kg), Raney Nickel (0.375 kg) and methanol (32.5 kg) are charged; and purged with nitrogen and vacuum several times and then with hydrogen plus vacuum 3 times. The pressure is adjusted to 4 bar and then heated to 70° C. The pressure is kept at 4 bar until no more hydrogen is consumed; followed by stirring at this temperature for 2 additional hours. The pressure and sample are released by the bottom valve. If reaction is not complete according to analysis, reheat to 70° C. under 4 bar H gas and stir another hour. If reaction is complete, clarify the reaction mixture through a cartridge filter. The solvent is removed by vacuum distillation (maximum 60° C.) and added to the residue toluene (44 kg) and acetone (121 kg). Over this mixture hydrochloric acid (3.7 kg) is added dropwise. The white solid is centrifuged and washed with acetone. This solid is dissolved in methanol (55 kg) at 60° C., and to this solution another one of sodium bicarbonate (3.95 kg) in water (165 kg) is added keeping the temperature below 60° C. 0.7 kg of carbon are added and the mixture is stirred at 60° C. for an hour. It is then clarified and cooled to 15-20° C. After stirring for one hour at this temperature, the mixture is centrifuged and washed twice with water. The solid is dried until the water content is below 0.5%. The expected amount it 5.5 kg (82.5% yield).

What is claimed is:

1. A process for preparing 5-(4-methyl-1H-imidazol-1-yl)-3-(trifluoromethyl)-benzenamine (I), comprising the steps of:
   a) reacting, in a coupling reaction, the compound

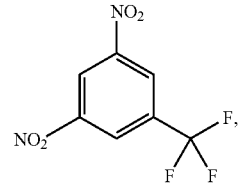

with 4-methyl-1H-imidazole (IIIa) to prepare 4-methyl-1-(3-nitro-5-trifluoromethyl-phenyl)-1H-imidazole (III); and b) reducing the resulting 4-methyl-1-(3-nitro-5-trifluoromethyl-phenyl)-1H-imidazole to produce the compound of formula (I).

2. The process according to claim 1, wherein Step a) is performed at a temperature in the range of 80-150° C.

3. The process according to claim 1, wherein Step a) is performed at a temperature in the range of 90-140° C.

4. The process according to claim 1, where the reduction reaction Step b) involves Group VIII metal catalysts, hydrogen gas or hydrogen transfer agents.

5. The process according to claim 4, where the catalyst is palladium, platinum or Raney Nickel or combinations thereof.

6. A process for preparing 5-(4-methyl-1H-imidazol-1-yl)-3-(trifluoromethyl)-benzenamine (I), comprising the steps of:
   a) reacting, in a suitable base using an appropriate solvent, the compound

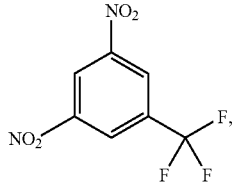

with 4-methyl-1H-imidazole to prepare 4-methyl-1-(3-nitro-5-trifluoromethyl-phenyl)-1H-imidazole (III); and
   b) hydrogenating the resulting 4-methyl-1-(3-nitro-5-trifluoromethyl-phenyl)-1H-imidazole (III) with hydrogen gas and a suitable catalyst using an appropriate solvent to produce the compound of formula (I).

7. A process according to claim 6, wherein the base is an alkoxide, a hydride, a carbonate or a phosphate.

8. The process according to claim 1, wherein Step a) utilizes a polar aprotic solvent selected from dimethyl sulfoxide (DMSO), dimethylformamide (DMF), diglyme, THF, N-methyl pyrrolidone (NMP) and dimethylacetamide (DMA).

9. A process according to claim 1, wherein microwaves are used.

10. A process according to claim 1, wherein a faster heating and cooling cycle is achieved by additional heat exchanger capacity in batch vessels or by using continuous reaction equipment to obtain higher selectivity.

* * * * *